(12) United States Patent  (10) Patent No.: US 8,962,694 B2
Dall et al.  (45) Date of Patent: Feb. 24, 2015

(54) COMPOSITION FOR PEST CONTROL

(75) Inventors: David James Dall, Downer (AU); Joan Dawes, Coogee (AU)

(73) Assignee: Pestat Pty Ltd., Bruce, Australian Capital Territory (AU)

( * ) Notice: Subject to any disclaimer, the term of this patent is extended or adjusted under 35 U.S.C. 154(b) by 971 days.

(21) Appl. No.: 12/312,500

(22) PCT Filed: Dec. 18, 2007

(86) PCT No.: PCT/AU2007/001955
§ 371 (c)(1),
(2), (4) Date: Oct. 7, 2009

(87) PCT Pub. No.: WO2008/074070
PCT Pub. Date: Jun. 26, 2008

(65) Prior Publication Data
US 2010/0069506 A1  Mar. 18, 2010

(30) Foreign Application Priority Data

Dec. 18, 2006  (AU) ................................ 2006907040

(51) Int. Cl.
*A01N 31/02*  (2006.01)
*A01N 31/08*  (2006.01)

(52) U.S. Cl.
CPC ..................................... *A01N 31/08* (2013.01)
USPC ............ 514/724; 514/731; 514/737; 424/405

(58) Field of Classification Search
CPC ............................... A01N 31/08; A01N 23/00
USPC ............................ 514/724, 731, 737; 424/405
See application file for complete search history.

(56) References Cited

FOREIGN PATENT DOCUMENTS

| AP | 000244 A | 3/1993 |
| AP | 244 A | 3/1993 |
| JP | 58021603 | 2/1983 |
| JP | 62106001 | 5/1987 |
| JP | 09020603 | 1/1997 |
| WO | WO 97/00609 | 1/1997 |

OTHER PUBLICATIONS http://www.au.gardenweb.com/forums/load/pests/msg0804303116332.html, Nasty toads—Pests & disease forum—Garden Web Aug. 2002.*
http://www.exploroz.com/Forum/Topic/39368/Cane_toads.aspx, Cane toads, Nov. 2006.*
"Cane Toad Trapping" (online), http://www.abc.net.au/farnorth/stories/s1290727.htm, Australian Broadcasting Corporation, 2005.
"So What Can Be Done About Toads?" (online), http://www.fdrproject.org/pages/TDdispose.htm, Frog Decline Reversal Project Inc., 2003.

* cited by examiner

*Primary Examiner* — Mina Haghighatian
(74) *Attorney, Agent, or Firm* — Klauber & Jackson LLC

(57) ABSTRACT

Compositions suitable for the control of pest amphibian species are described. More particularly, compositions for killing amphibians are described that comprise:
(i) a xylenol compound or derivative according to formula (I)

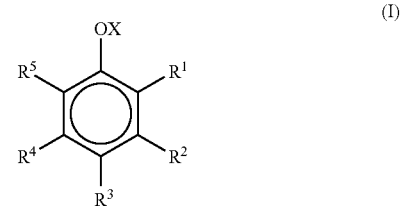

wherein
$R^1, R^2, R^3, R^4$ and $R^5$ are each independently selected from hydrogen, hydroxyl, halogen, $-NH_3$ and $C_{1-6}$ alkyl, and $-R^6-NH_2$, $-R^6-ONH_2$, $-R^6-NO_2$, and $-R^6-PO_4$, wherein $R^6$ is $C_{1-6}$ alkyl, and
X is selected from hydrogen, halogen and $C_{1-6}$ alkyl,
or a salt thereof, and
(ii) ethanol and optionally,
(iii) methanol and/or at least one $C_{3-6}$ alcohol.
Methods for killing amphibians include contacting the amphibian with said compositions. Kits are described wherein said xylenol compounds and ethanol and optionally methanol and/or at least one $C_{3-6}$ alcohol may be administered simultaneously or sequentially.

4 Claims, 2 Drawing Sheets

COMPOSITION FOR PEST CONTROL

CROSS REFERENCE TO RELATED APPLICATIONS

The present application is a National Stage Application claiming the priority of co-pending PCT Application No. PCT/AU2007/001955 filed Dec. 18, 2007, which in turn, claims priority from Australian application Serial No. 2006907040 filed Dec. 18, 2006. Applicants claim the benefits of 35 U.S.C. §120 as to the PCT application and priority under 35 U.S.C. §119 as to the said Australian application, and the entire disclosures of both applications are incorporated herein by reference in their entireties.

FIELD OF THE INVENTION

The present invention relates to a pesticidal composition for use on amphibians, methods of use and kits thereof. More particularly, the invention relates to a pesticidal composition for use on amphibians comprising a xylenol compound or derivative thereof in combination with one or more alcohol carriers.

BACKGROUND OF THE INVENTION

Pest organisms have a detrimental impact on the areas they infest, and commonly cause economic, environmental and/or social problems. As a consequence there is ongoing demand for safe, humane and effective methods for their management and control.

Organisms ranging from invertebrate herbivores such as snails and caterpillars to vertebrate predators such as foxes, coyotes and feral cats are considered to be pests in different parts of the world. A number of amphibians are also considered to be pest organisms; these include species such as the cane toad (*Bufo marinus*), the Cuban tree frog (*Osteopilus septentrionalis*), the American bullfrog (*Lithobates catesbeiana*) and the coqui frog (*Eleutherodactylus coqui*). Each of these amphibian species has significant impacts in areas they infest, with effects that include displacement of native amphibia, poisoning of native wildlife and domestic animals, and loss of social amenity.

The cane toad (*Bufo marinus*) is a significant pest in Australia, continental USA, and various other Pacific and Caribbean locations. The cane toad was deliberately introduced into Australia in 1935 in an attempt to control beetle pests of sugarcane in northern Queensland (Lever, C., 2001). The toad established effectively at points of release, but proved completely ineffective with respect to its intended role. Since then the cane toad has spread widely across the Australian continent, such that its distribution now extends from northern New South Wales, through coastal and northern regions of Queensland, and into the western parts of the Northern Territory. Isolated populations are also found in various urban centres such as Katherine, where toads apparently rely on the suitable habitat associated with water in parks, gardens and recreational areas. It is expected that the distribution of the toad will continue to extend westwards across northern Australia, to ultimately cover the entire "Top End" of the continent, including the Kimberley and the Ord River regions. Some authorities have also suggested that the toad has the potential to colonise the warmer northern regions of the Murray-Darling basin.

Establishment of the cane toad is considered to have significantly impacted the Australian environment. In this regard, the cane toad's capabilities as a predator of native invertebrates and a competitor of native amphibia, together with its capacity to poison reptiles and other animals by which it is mouthed or ingested, are believed to have significantly affected endemic species in freshwater and riparian settings (Doody, J. S. et al., 2006). The biotic impact of cane toads has recently been listed under the Commonwealth *Environment Protection and Biodiversity Act* (EPBC Act) as a "key threatening process" to the Australian environment.

Cane toads were also deliberately released in Florida, also in attempts to control insect pests of sugarcane. In addition, an accidental release at Miami International Airport appears to have been important for their establishment in the state (Youth, H., 2005). In the USA, as in Australia, the cane toad consumes, competes with, and poisons native wildlife.

In both Australia and the USA, the cane toad also has a detrimental impact on the "quality of life" in urban settings, where its presence in areas such as domestic yards and parkland areas poses a threat of poisoning to domestic pets (Roberts, B. K. et al., 2000; Reeves, M. P., 2004), and a risk that children may be exposed to the toxin of the pest.

Another significant amphibian pest in south-eastern USA is the Cuban tree frog (*Osteopilus septentrionalis*). The frog is thought to have been introduced into Florida from its area of endemicity in the Caribbean by accidental transport in shipping crates (Johnson, S. A. 2007). The species has now expanded its range to include much of Florida, and individuals have also been found in the state of Georgia (Knapp, W. W., 2007).

As with cane toads, Cuban tree frogs have "negative impacts on Florida's native species and ecosystems" (Johnson, S. A., 2007), principally because of their competitive capabilities and predatory behaviour. Cuban tree frogs also secrete a material that coats their skin and that is "extremely irritating" to the eyes and nose of persons (Johnson, S. A., 2007). Cuban tree frogs also impact on social amenity through their propensity to shelter in houses, and in other structures such as electrical transformer boxes, from where they can cause short-circuits and resultant power outages to the surrounding area (Johnson, S. A., 2007).

Two other invasive amphibian species are also worthy of note, having, like the cane toad, been nominated by the Invasive Species Specialist Group (ISSG) as members of the "World's Worst Invasive Alien Species" (International Union for the Conservation of Nature ISSG, 2006). These species are *Eleutherodactylus coqui* (the "coqui", a small tree frog native to Puerto Rico) and *Rana catesbeiana*, the North American bullfrog.

Humane ways of killing pest amphibia are not available to most householders, either because they involve the need for restricted drugs or poisons or a degree of specialist training. Gassing and freezing are commonly used methods for killing amphibia; each, however, requires physical handling and the transportation of live animals, which can pose a risk to handlers. Further, these methods can be difficult to conduct in remote settings. While freezing is the recommended method for destroying cane toads in domestic settings in some jurisdictions, most householders find freezing undesirable due to the possibility of contamination of food with the toxin. As a consequence, a variety of broadly unacceptable "techniques", commonly involving physical violence, are adopted, particularly for cane toad control. Outcomes of these methods can be uncertain, and the use of violent means of control is considered to be socially unacceptable by a large segment of the population. In addition, there are reports of persons being adversely affected by toad toxins in the course of attempting to kill the animals (Wilson, A., 2006). This can be explained, in many cases, by discharge of the toxin following dubbing of the animal, and subsequent contact with and poisoning through the skin or mucosal surfaces.

To overcome these problems there is growing interest in the use of various forms of traps to catch pest amphibia, such as cane toads (Sawyer, G., 2006). While some of these can apparently operate effectively, captured amphibia must still be killed by some means.

Against this background, it can be appreciated that a method of killing pest amphibians such as cane toads and Cuban tree frogs in an acceptable timeframe, while providing a humane mode of action and convenience of use, would provide a valuable advance in efforts to manage the pests.

The present applicant proposes herein a pesticidal composition for use on pest amphibians that is relatively safe to use, that may be suitable for household use and which, in addition, removes the need for specialist equipment and/or training in order to apply. Further, in the contexts of cane toad and Cuban tree frog control, the proposed pesticidal composition removes the risk of harm from exposure to the cane toad toxin to those who would normally use physical means to destroy the animals.

SUMMARY OF THE INVENTION

In a first aspect, the present invention provides a composition for killing amphibians comprising:

(i) a xylenol compound or derivative according to formula (I)

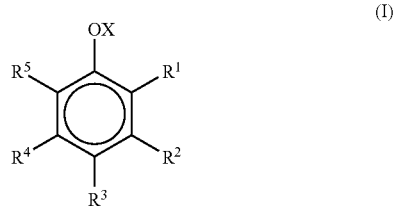

wherein $R^1$, $R^2$, $R^3$, $R^4$ and $R^5$ are each independently selected from hydrogen, hydroxyl, halogen, —$NH_3$ and $C_{1-6}$ alkyl, and —$R^6$—$NH_2$, —$R^6$—$ONH_2$, —$R^6$—$NO_2$, and —$R^6$—$PO_4$, wherein $R^6$ is $C_{1-6}$ alkyl, and X is selected from hydrogen, halogen and $C_{1-6}$ or a salt thereof;

(ii) ethanol; and optionally, (iii) methanol and/or at least one $C_{3-6}$ alcohol.

Compositions may further comprise at least one compound selected from diluents, solvents, thickeners, stablisers, propellants, fragrants, insecticides, insect repellants, amphibian attracting agents or canine or feline repelling agents.

Compositions according to the first aspect may consist of (i) a xylenol compound or derivative according to formula (I)

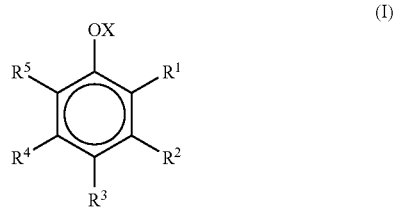

wherein $R^1$, $R^2$, $R^3$, $R^4$ and $R^5$ are each independently selected from hydrogen, hydroxyl, halogen, —$NH_3$ and $C_{1-6}$ alkyl, and —$R^6$—$NH_2$, —$R^6$—$ONH_2$, —$R^6$—$NO_2$, and —$R^6$—$PO_4$, wherein $R^6$ is $C_{1-6}$ alkyl, and X is selected from hydrogen, halogen and $C_{1-6}$ alkyl, or a salt thereof;

(ii) ethanol; and optionally, (iii) methanol and/or at least one $C_{3-6}$ alcohol.

Preferably, $R^1$, $R^2$, $R^3$, $R^4$ and $R^5$ are each independently selected from hydrogen, halogen, —$NH_3$ and $C_{1-6}$ alkyl. Any two of $R^1$, $R^2$, $R^3$, $R^4$ and $R^5$ may be —$CH_3$. Any one of $R^1$, $R^2$, $R^3$, $R^4$ and $R^5$ may be selected from Cl and Br. X may optionally be H.

More preferably, the xylenol compound is chloroxylenol or a salt thereof. The composition may optionally comprise a xylenol compound or derivative wherein $R^1$ and $R^5$ are hydrogen, $R^2$ and $R^4$ are $C_{1-6}$ alkyl (especially, $C_{1-3}$ alkyl) and may be the same or different, $R^3$ is hydrogen or halogen (especially, Cl and Br), and X is hydrogen, or a salt thereof.

In one especially preferred embodiment, the composition comprises a xylenol compound or derivative wherein $R^1$ and $R^5$ are hydrogen, $R^2$ and $R^4$ are both methyl, $R^3$ is Cl, and X is hydrogen (i.e. 4-chloro 3,5-dimethyl phenol), or a salt thereof.

The composition comprises ethanol and, preferably, at least one additional alcohol selected from methanol and C alcohols. Preferably, the at least one additional alcohol is selected from methanol, propanol (such as isopropanol), and mixtures thereof. Most preferably, the composition comprises ethanol in admixture with methanol or, most preferably, propanol. The ethanol and the optional additional alcohol(s) may be provided in the composition as an aqueous solution (e.g. a 10% to 50% aqueous solution).

For mixtures of ethanol and propanol, it is preferred that the mixtures comprise ethanol at a concentration greater than about 50% (based upon the total volume of alcohol) and propanol at a concentration less than about 50% (based upon the total volume of alcohol).

Preferably, the composition comprises a xylenol compound or derivative according to formula (I) at a concentration of between 0.1% and 10% (w/v), more preferably between 0.5% and 6.5% (w/v), and a mixture of ethanol (at a concentration of greater than 50% based upon the total volume of alcohol) and propanol (at a concentration of less than 50% based upon the total volume of alcohol).

More preferably, ethanol may be present at a concentration of between about 55% (v/v) and about 80% (v/v), and isopropanol may be present at a concentration of between about 20% (v/v) and about 40% (v/v).

Most preferably, compositions comprise:

(i) 4-chloro 3,5-dimethyl phenol at a concentration of about 4.0% (w/v);

(ii) ethanol at a concentration of about 67% (v/v);

(iii) isopropanol at a concentration of about 30% (v/v); and (iv) citral at a concentration of about 0.5% (v/v).

In a second aspect, the present invention provides a method for killing an amphibian, said method comprising contacting the amphibian with:

(i) a xylenol compound or derivative according to formula (I)

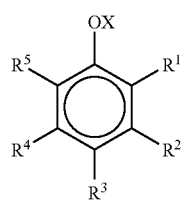

(I)

wherein $R^1, R^2, R^3, R^4$ and $R^5$ are each independently selected from hydrogen, hydroxyl, halogen, —$NH_3$, and $C_{1-6}$ alkyl, and —$R^6$—$NH_2$, —$R^6$—$ONH_2$, —$R^6$—$NO_2$, and —$R^6$—$PO_4$, wherein $R^6$ is $C_{1-6}$ alkyl, and X is selected from hydrogen, halogen and $C_{1-6}$ alkyl, or a salt thereof; and (ii) ethanol; and optionally, (iii) methanol and/or at least one C alcohol.

Optionally, said xylenol compound or derivative is chloroxylenol or a salt thereof. Further, said ethanol, optionally in admixture with methanol and/or at least one $C_{3-6}$ alcohol, may be brought into contact with the amphibian sequentially or simultaneously.

Preferably, the xylenol compound or derivative and the ethanol, optionally in admixture with methanol and/or at least one $C_{3-6}$ alcohol, are brought into contact with the amphibian simultaneously.

The xylenol compound and the ethanol are preferably delivered topically which may include delivery by aerosol, liquid spray, dip, dripper, wipe, brush or absorbant support.

In a third aspect, the present invention provides for a kit for killing amphibians comprising:

(i) a xylenol compound or derivative according to formula (I)

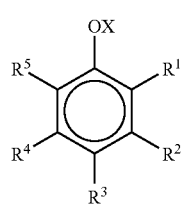

(I)

wherein $R^1, R^2, R^3, R^4$ and $R^5$ are each independently selected from hydrogen, hydroxyl, halogen, —$NH_3$ and $C_{1-6}$ alkyl, and —$R^6$—$NH_2$, —$R^6$—$ONH_2$, —$R^6$—$NO_2$, and —$R^6$—$PO_4$, wherein $R^6$ is $C_{1-6}$ alkyl, and X is selected from hydrogen, halogen and $C_{1-6}$ alkyl, or a salt thereof;

(ii) ethanol; and optionally, (iii) methanol and/or at least one C alcohol.

Preferably, the kit comprises a xylenol compound which is chloroxylenol or a salt thereof.

The kit may provide the xylenol compound or derivative thereof, the ethanol, and, if provided, the methanol and/or at least one $C_{3-6}$ alcohol, in the same or separate packaging (e.g. one or more tubes, bottles or other containers).

The xylenol compound and the ethanol may be provided within a handheld sprayer, a larger spray pack, a bait or an absorbent support.

DETAILED DESCRIPTION OF THE INVENTION

Figure 1:
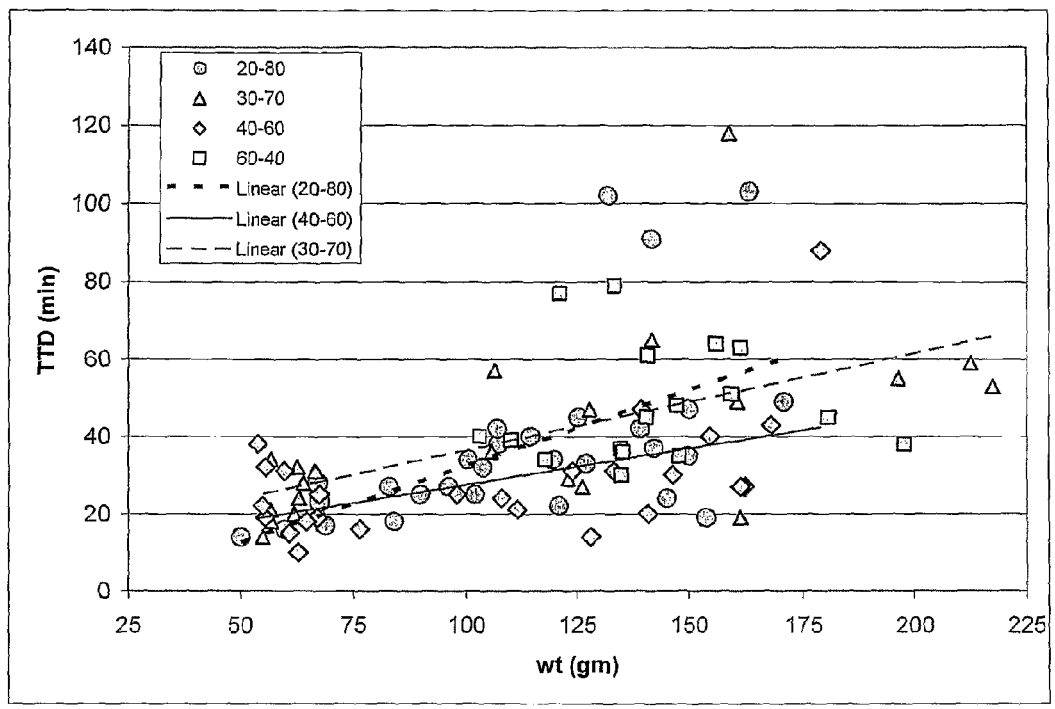
FIG. 1 shows the treatment of cane toads with chloroxylenol in an ethanol/propanol carrier where the carrier mixtures tested were 80% ethanol with 20% isopropanol (20-80), 70% ethanol with 30% isopropanol (30-70), 60% ethanol with 40% isopropanol (40-60), and 40% ethanol with 60% isopropanol (60-40) (three different concentrations of chloroxylenol were used in the tests). The axes show weight of cane toads in grams (x-axis) and the minutes to death post-treatment (y-axis).

The present applicant has found that a humane pesticidal composition for controlling cane toads and other amphibians can be achieved by contacting the amphibian with a pesticidal agent (i.e. killing agent), an anaesthetising agent and an appropriate carrier. Further, the present applicant has surprisingly found that the anaesthetising agent can be a $C_{1-6}$ alcohol (preferably, ethanol alone or in admixture with at least one additional alcohol), and that such alcohols and mixtures thereof, are also suitable for use as carriers for certain pesticidal agents, namely xylenol compounds and derivatives thereof. The pesticidal composition may be formulated such that it is relatively safe to handle and can be easily administered to pest amphibians such as cane toads and Cuban tree frogs.

In a first aspect, the present invention provides a composition for killing amphibians comprising:

(i) a xylenol compound or derivative according to formula (I)

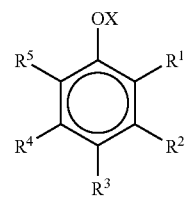

(I)

wherein $R^1, R^2, R^3, R^4$ and $R^5$ are each independently selected from hydrogen, hydroxyl, halogen, —$NH_3$ and $C_{1-6}$ alkyl, and —$R^6$—$NH_2$, —$R^6$—$ONH_2$, —$R^6$—$NO_2$, and —$R^6$—$PO_4$, wherein $R^6$ is $C_{1-6}$ alkyl, and X is selected from hydrogen, halogen and $C_{1-6}$ alkyl,
or a salt thereof;
(ii) ethanol; and optionally,
(iii) at least one C alcohol.

The xylenol compound or derivative thereof provides the composition with a pesticidal agent. The particular xylenol compound or derivative thereof may be selected on the basis of relative efficacy in killing a target pest amphibian species. Such efficacy may vary where it is desirable to kill pest amphibians of a certain size or range of sizes. Further, the particular xylenol compound or derivative thereof may be selected on the basis of relative stability in a specific environment or suitability for a desired mode of administration.

Preferably, $R^1$, $R^2$, $R^3$, $R^4$ and $R^5$ are each independently selected from hydrogen, halogen, —$NH_3$ and $C_{1-6}$ alkyl. Any two of $R^1$, $R^2$, $R^3$, $R^4$ and $R^5$ may be —$CH_3$. Any one of $R^1$, $R^2$, $R^3$, $R^4$ and $R^5$ may be selected from Cl and Br. X may optionally be H.

More preferably, the xylenol compound is chloroxylenol or a salt thereof. The composition may optionally comprise a xylenol compound or derivative thereof wherein $R^1$ and $R^5$ are hydrogen, $R^2$ and $R^4$ are $C_{1-6}$ alkyl (especially, $C_{1-3}$ alkyl) and may be the same or different, $R^3$ is hydrogen or halogen (especially, Cl and Br), and X is hydrogen, or a salt thereof.

In one especially preferred embodiment, the composition comprises a xylenol compound or derivative wherein $R^1$ and $R^5$ are hydrogen, $R^2$ and $R^4$ are both methyl, $R^3$ is Cl, and X is hydrogen (i.e. 4-chloro 3,5-dimethyl phenol), or a salt thereof.

In another especially preferred embodiment, the composition comprises a xylenol compound or derivative wherein $R^1$ and $R^5$ are hydrogen, $R^2$ and $R^4$ are both methyl, $R^3$ is hydrogen, and X is hydrogen (i.e. 3,5-dimethyl phenol), or a salt thereof.

The composition comprises ethanol and, preferably, at least one additional alcohol selected from methanol and $C_{3-6}$ alcohols. Preferably, the at least one additional alcohol is selected from methanol, propanol (such as isopropanol), and mixtures thereof. More preferably, the composition comprises ethanol in admixture with methanol or, most preferably, propanol. The ethanol and the optional additional alcohol(s) may be provided in the composition as an aqueous solution (e.g. a 10% to 50% aqueous solution).

For mixtures of ethanol and propanol, it is preferred that the mixture comprises ethanol at a concentration greater than about 50% (based upon the total volume of alcohol) and propanol at a concentration less than about 50% (based upon the total volume of alcohol).

Preferably, the composition comprises a xylenol compound or derivative according to formula (I) at a concentration of between 0.1% and 10% (by volume), more preferably between 0.5% and 5% (by volume), and a mixture of ethanol (at a concentration of greater than 50% based upon the total volume of alcohol) and propanol (at a concentration of less than 50% based upon the total volume of alcohol).

More preferably, the composition comprises 4-chloro 3,5-dimethyl phenol at a concentration of between 0.5% and 6.5% (by volume), and a mixture of ethanol (at a concentration of about 70% based upon the total volume of alcohol) and propanol (at a concentration of about 30% based upon the total volume of alcohol).

More preferably, ethanol may be present at a concentration of between about 55% (v/v) and about 80% (v/v), and isopropanol may be present at a concentration of between about 20% (v/v) and about 40% (v/v).

Most preferably, compositions comprise:

(i) 4-chloro 3,5-dimethyl phenol at a concentration of about 4.0% (w/v);
(ii) ethanol at a concentration of about 67% (v/v);
(iii) isopropanol at a concentration of about 30% (v/v); and
(iv) citral at a concentration of about 0.5% (v/v).

The composition may also comprise additional agents such as, for example, appropriate diluents, solvents, thickeners, stablisers, propellants or other agents to assist in aerosolising the composition, and other excipients as appropriate for the particular pesticidal agent (i.e. xylenol compound or derivative thereof) and the mode of administration. Further, the composition may also comprise fragrants, insecticides or insect repellants (e.g. citral). Alternatively or additionally, other agents such as amphibian attracting agents or canine or feline repelling agents may be included in the composition of the present invention.

The composition is particularly suitable for use in killing cane toads and Cuban tree frogs (e.g. for use in the control of these species in Australia and elsewhere, such as USA and Brazil, where they have also become pest species). The composition, however, may also be suitable for killing other species of pest amphibians such as the Coqui (*Eleutherodactylus coqui*) which is a pest species in Hawaii, and the American bullfrog which is a known or potential pest in many locations outside its natural range, including western USA, Hawaii, Brazil and Europe (Crayon, J. J., 2005; Giovanelli, J. G. R. et al., 2007; Ficetola, G. F. et al., 2007).

In a particularly preferred embodiment, the composition consists of:

(i) 4-chloro 3,5-dimethyl phenol at a concentration of about 4.0% (w/v);
(ii) ethanol at a concentration of about 67% (v/v);
(iii) isopropanol at a concentration of about 30% (v/v); and
(iv) citral at a concentration of about 0.5% (v/v).

In a second aspect, the present invention provides a method for killing amphibian, said method comprising contacting the amphibian with:

(i) a xylenol compound or derivative according to formula (I)

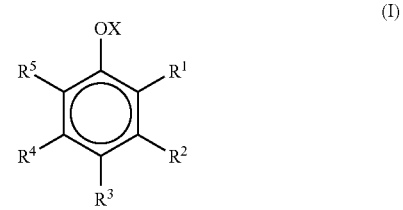

wherein
$R^1$, $R^2$, $R^3$, $R^4$ and $R^5$ are each independently selected from hydrogen, hydroxyl, halogen, —$NH_3$ and $C_{1-6}$ alkyl, and —$R^6$—$NH_2$, —$R^6$—$ONH_2$, —$R^6$—$NO_2$, and —$R^6$—$PO_4$, wherein $R^6$ is $C_{1-6}$ alkyl, and
X is selected from hydrogen, halogen and $C_{1-6}$ alkyl,
or a salt thereof; and
(ii) ethanol, optionally in admixture with methanol and/or at least one $C_{3-6}$ alcohol,
wherein said xylenol compound or derivative and said ethanol, optionally in admixture with methanol and/or at least one $C_{3-4}$ alcohol, may be brought into contact with the amphibian sequentially or simultaneously.

Preferably, the said xylenol compound or derivative and said ethanol, optionally in admixture with methanol and/or at least one $C_{3-6}$ alcohol, are brought into contact with the amphibian simultaneously.

Accordingly, the method preferably involves contacting the amphibian with a composition according to the first aspect of the present invention. Preferably, the composition is brought into contact with the amphibian by topical administration.

This may be achieved through means including, but not limited to, direct topical application of the composition to the amphibian by the user, for example, by brushing the composition onto the dorsal surface of the amphibian or, more conveniently, by spraying the composition onto the dorsal surface of the amphibian. Accordingly, the composition may preferably be provided as a liquid pump spray or aerosol formulation. Particularly suitable spray formulations include formulations for administration as an aerosol spray (either via a handheld sprayer e.g. an aerosol can, a larger domestic spray pack, a truck sprayer or a crop duster).

Alternatively, topical administration may also be achieved by indirect means requiring no manual application. For example, an absorbant support may be continuously infused with the composition of the present invention such that it is applied to the amphibian when the amphibian comes into contact with the support. Such a support can be incorporated into other structures in a manner whereby an amphibian will contact the composition when moving through or into the structure (e.g. the support may be present on flaps or other elements of a trap that may be contacted by an amphibian). Alternatively, the composition of the present invention may be used to fill a bath residing in the base of a trap, or used as a liquid spray or aerosol formulation in a mechanism whereby an amphibian can trigger the spraying of the composition.

In a third aspect, the present invention provides for a kit for killing amphibians comprising:

(i) a xylenol compound or derivative according to formula (I)

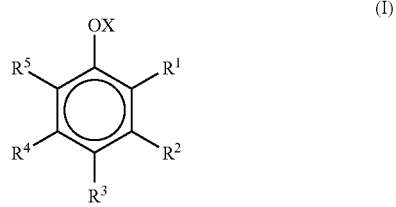

wherein $R^1$, $R^2$, $R^3$, $R^4$ and $R^5$ are each independently selected from hydrogen, hydroxyl, halogen, —$NH_3$ and $C_{1-6}$ alkyl, and —$R^6$—$NH_2$, —$R^6$—$ONH_2$, —$R^6$—$NO_2$, and —$R^6$—$PO_4$, wherein $R^6$ is $C_{1-6}$ alkyl, and X is selected from hydrogen, halogen and $C_{1-6}$ alkyl, or a salt thereof;

(ii) ethanol; and optionally, (iii) methanol and/or at least one $C_{3-6}$ alcohol.

The kit may provide the xylenol compound or derivative thereof, the ethanol, and, if provided, the methanol and/or at least one $C_{3-6}$ alcohol, in the same or separate packaging (e.g. one or more tubes, bottles or other containers).

The kit may also include one or more delivery systems for the xylenol compound or derivative thereof, the ethanol, and the optional additional alcohol(s) such as, for example, a handheld sprayer (e.g. a trigger sprayer or an aerosol can) or a larger, domestic spray pack. Alternatively, the kit may include an absorbant support delivery system or automated delivery system as described above.

Delivery systems may also be provided for compositions according to the first aspect or methods according to the second aspect.

It is further envisaged that the present invention may be combined with other forms of pest amphibian control such as, for example, trapping, baiting, and other forms of poisoning.

The present invention is hereinafter further described by way of the following, non-limiting examples and accompanying figures.

EXAMPLES

The trials described in the following Examples 1, 2 and 3 were conducted on cane toads sourced from field populations in northern Queensland, Australia. Trials in Example 4 were conducted on cane toads and Cuban tree frogs sourced from the field in Florida, USA.

Example 1

Testing of Pesticidal Agents Following Anaesthesia Induced with an Anaesthetising Agent In the course of preliminary testing compounds for the lethal control of amphibians, it had surprisingly been found that ethanol was able to act as a rapid- and long-acting anaesthetic for cane toads, and noted that its topical application reliably and rapidly induced loss of coordination and general stupefaction of the toads. This effect was seen in toads of all sizes. However, the application of ethanol on cane toads was found to be generally ineffective in the extermination of the animals. That is, it was observed that ethanol was capable of causing death only in some (but not all) very small toads (i.e. toads of less than about 45 gm in weight).

Materials and Methods

Trial 1

Testing of the efficacy of various compositions for the purpose of cane toad extermination was conducted in two trials. The first trial comprised a "two-step" test in which subject toads were initially exposed to an anaesthetic agent and, once anaesthetised, exposed to a pesticidal agent (i.e. killing agent) in the presence of a suitable carrier. This two-step approach was undertaken to ensure the humane extermination of the animals.

Subject animals were therefore exposed to an approximate total dose of 3-4 ml of materials, comprising 2-3 gm of an anaesthetising agent (i.e. ethanol) and up to 1.0 ml of the particular pesticidal agent to be tested. A mist of ethanol was applied ("primary treatment") to the dorsal surface of the toad from a hand-held spray bottle. When the toad was stupefied, as judged by the inability of the animal to right itself onto its ventral surface when turned onto its back (generally 10-15 minutes after treatment), the test pesticidal agent was administered ("secondary treatment") onto the animal's dorsal surface by means of a micropipette. The test pesticidal agent included chloroxylenol (i.e. 4-chloro 3,5-dimethyl phenol) in different carriers including ethanol, isopropanol, propanol and dilute solutions thereof. Animals were monitored continuously for their response to the treatment.

Results and Discussion

The results of Trial 1 are presented in Table 1. These results showed that chloroxylenol in carriers (i.e. ethanol alone or dilutions of propanol) resulted in the extermination of all 12 ethanol-anaesthetised toads to which the pesticidal agent formulations were administered. In contrast, control treatments with ethanol alone and treatments with isopropanol as the carrier resulted in the death of only 1 of 14 toads tested; the only death occurring in one of the smallest toads used in any of the tests (40.4 gm in weight). Therefore, it is evident that chloroxylenol can be an effective pesticidal agent to cane toads, and that its lethal effect can be modulated via administration with a range of carrier compounds.

TABLE 1

Effect of treatment of cane toads with chloroxylenol in different carriers

| Treatment | | Toad size class | | |
|---|---|---|---|---|
| Primary | secondary | Very small (<45.0 gm) | Small (45.0-89.9 gm) | Medium (90.0-139.9 gm) |
| 100% ethanol; 2.1-2.9 ml | — | 1/2[1]; 38[2] | 0/1; n.a. | 0/3; n.a. |
| 100% ethanol; 2.1-2.9 ml | 100% ethanol; 0.5 ml | | 0/2; n.a. | |
| 100% ethanol; 2.1-2.9 ml | 30% chloroxylenol in ethanol; 0.5 ml | | 2/2; 64 | |
| 100% ethanol; 2.1-2.9 ml | 30% chloroxylenol in ethanol; 0.2 ml | | 2/2; 71 | |
| 100% ethanol; 2.1-2.9 ml | 100% isopropanol; 0.5 ml | | 0/1; n.a. | 0/1; n.a. |
| 100% ethanol; 3.2 ml | 100% isopropanol; 1.0 ml | | | 0/2; n.a. |
| 100% ethanol, 2.1 ml | 60% isopropanol/40% water; 1.0 ml | | 0/2; n.a. | |
| 100% ethanol, 2.1 ml | 15% chloroxylenol in 60% isopropanol/40% water; 1.0 ml | | 2/2; 24 | |
| 100% ethanol, 2.1-2.9 ml | 5% chloroxylenol in 40% isopropanol/ 60% water; 1.0 ml | | 5/5; 30 | 1/1; 28 |

[1] number died/number tested.
[2] mean time to death (minutes).

Example 2

Testing of Pesticidal Agents in Combination with an Anaesthetising Agent

The observed difference in lag period before the onset of the anaesthetising agent (between 10-15 minutes) and the onset of death (16-102 minutes) in the "two-step" tests of Example 1, indicate that ethanol is faster acting as an anaesthetic than is chloroxylenol as a pesticidal agent. Therefore, it was envisaged that a "single step" test could be developed in which ethanol and chloroxylenol could be combined into a single composition (e.g. in a composition suitable for use as a spray, for ease of administration), while still achieving the humane extermination of cane toads.

Materials and Methods
Trial 2

The tests conducted in the second trial involved a single spray application of various test pesticidal compositions on cane toads. A hand-operated spray bottle was used to deliver a single standard dose of 3.0-3.3 gm of the particular test pesticidal agent to the dorsal surface of each animal. Animals were subsequently continuously monitored for their response to the treatment.

Results and Discussion

Tables 2, 3 and 4 summarise the outcomes of the Trial 2 tests on small, medium and large toads, respectively. Tables 3 and 4, in particular, summarise the results of tests on larger toads involving chloroxylenol in combination with ethanol and propanol.

As shown in Table 2, the inclusion of as little as 0.5% chloroxylenol in ethanol was sufficient to kill a (54.9 g) toad administered with the standard dose, although this treatment was effective for approximately only one third of the toads tested in this manner. In contrast, every toad classed as small (45-89.9 g) exposed to any test pesticidal agent composition including at least 2.5% chloroxylenol was killed by the treatment. In tests where ethanol was used as a sole carrier, or where mixtures of ethanol and propanol were used, mean times to death were less than 30 minutes. Use of mixtures in which water or methanol comprised a proportion of the carrier resulted in somewhat increased times to death; in the case of methanol, the stupefied toads also displayed some twitching of muscles and digits that were considered likely to be potentially unacceptable to users of the invention. Controls involving the administration of carrier solutions alone, as expected, did not result in toad death.

Table 2 also shows data relating to the incorporation of the fragrant/insect repellent agent, citral, into the test pesticidal agent compositions. In particular, it is shown that the inclusion of 2% citral in a 2.5% chloroxylenol formulation comprising 98% ethanol as a carrier does not hinder the efficacy of the composition, as all three toads tested were killed with an average time to death of 25 minutes. Comparatively, compositions comprising 2.5% chloroxylenol and 100% ethanol carrier showed a mean time to death of 28 minutes while the citral formulation showed the same time to death as the most effective carrier composition tested.

It is therefore possible to incorporate fragrants, insecticides or insect repellents to the compositions of the present invention without hindering the cane toad-killing efficacy.

As shown in Table 3, treatment with various pesticidal agent compositions comprising 2.5% or more chloroxylenol killed all 33 medium-sized toads to which they were applied. The same compositions also killed 31/32 large toads (Table 4); the exception to 100% success was one very large toad (188 gm) that was not killed by treatment with 3.75% chloroxylenol in a carrier comprising 80% ethanol with 20% propanol.

TABLE 2

Effect of treatment of small toads (45.0-89.9 gm) with chloroxylenol in different carriers

| carrier | Chloroxylenol content (%) | | | | |
|---|---|---|---|---|---|
| | 0.00 | 0.50 | 2.50 | 3.75 | 5.00 |
| 100% ethanol | 0/3[1]; n.a.[2] | 1/3; 62 | 3/3; 28 | — | 3/3; 22 |
| 80% ethanol with 20% isopropanol | — | — | 2/2; 25 | 4/4; 22 | 2/2; 16 |
| 70% ethanol with 30% isopropanol | 0/3; n.a. | — | 3/3; 26 | 3/3; 26 | 3/3; 22 |
| 60% ethanol with 40% isopropanol | 0/3; n.a. | — | 3/3; 27 | 3/3; 19 | 5/5; 21 |

TABLE 2-continued

Effect of treatment of small toads (45.0-89.9 gm) with chloroxylenol in different carriers

| carrier | Chloroxylenol content (%) | | | | |
|---|---|---|---|---|---|
| | 0.00 | 0.50 | 2.50 | 3.75 | 5.00 |
| 70% ethanol with 30% methanol | 0/3; n.a. | — | 3/3; 38 | — | — |
| 70% ethanol in water | — | — | 3/3; 46 | — | — |
| 98% ethanol with 2% citral | 0/3; n.a. | — | 3/3; 25 | — | — |

[1] number died/number tested.
[2] mean time to death (minutes).
n.a. not available.

TABLE 3

Effect of treatment of medium size toads (90.0-139.9 gm) with chloroxylenol in different carriers

| carrier | Chloroxylenol content (%) | | | |
|---|---|---|---|---|
| | 2.00 | 2.50 | 3.75 | 5.00 |
| 80% ethanol with 20% isopropanol | — | 5/5[1]; 37[2] | 4/4; 31 | 4/4; 52 |
| 70% ethanol with 30% isopropanol | 5/5; 65 | 5/5; 39 | — | — |
| 60% ethanol with 40% isopropanol | — | — | — | 7/7; 28 |
| 40% ethanol with 60% isopropanol | — | — | 4/4; 48 | 4/4; 46 |

[1] number died/number tested.
[2] mean time to death (minutes).

TABLE 4

Effect of treatment of large toads (≥140 gm) with chloroxylenol in different carriers

| carrier | Chloroxylenol content (%) | | | | |
|---|---|---|---|---|---|
| | 1.25 | 2.00 | 2.50 | 3.75 | 5.00 |
| 80% ethanol with 20% isopropanol | — | — | 1/1[1]; 91[2] | 3/4; 34 | 4/4; 53 |
| 70% ethanol with 30% isopropanol | 0/7; n.a. | 7/7; 50 | 7/7; 60 | — | — |
| 60% ethanol with 40% isopropanol | — | — | — | — | 7/7; 39 |
| 40% ethanol with 60% isopropanol | — | — | — | 5/5; 52 | 4/4; 47 |

[1] number died/number tested.
[2] mean time to death (minutes).
n.a. not available.

As shown in Table 4, a standard dose of a pesticidal agent composition comprising 1.25% chloroxylenol failed to kill any of the 7 large toads on which it was tested. In contrast, a composition comprising 2.0% chloroxylenol killed 7/7 large toads as well as 5/5 medium-sized toads (Table 3) to which it was administered. These results are consistent with observations based on the efficacy of 0.5% chloroxylenol on small toads; they also indicate that cane toads of larger size are likely to be more resistant than small toads with respect to efforts directed towards their lethal control.

Figure 2:
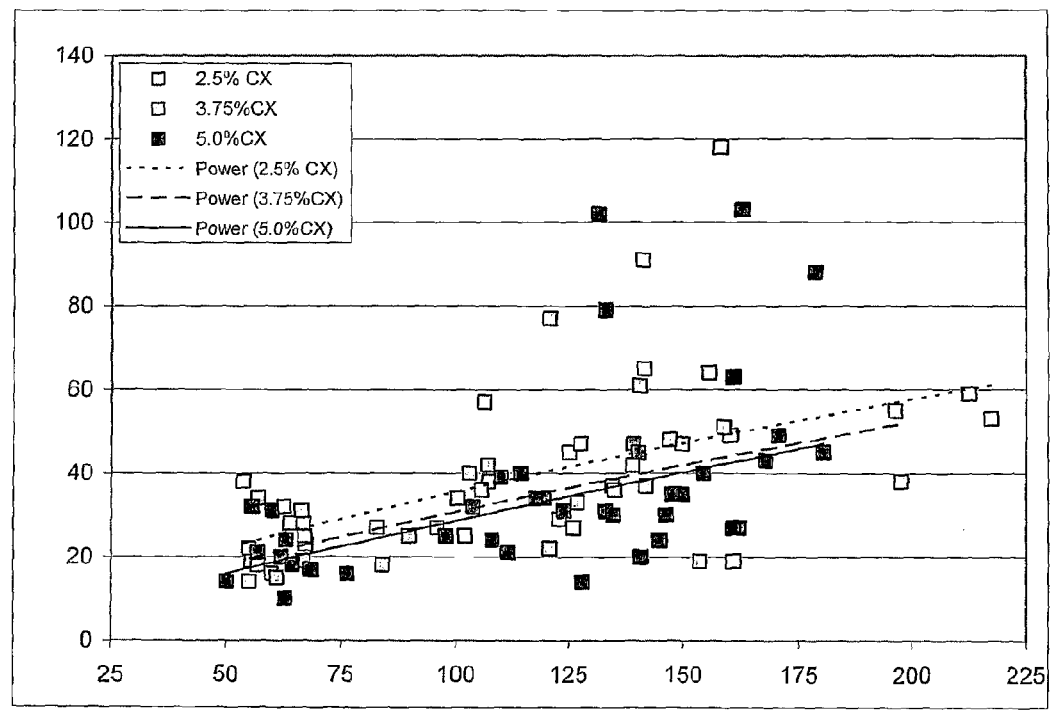
FIG. 2 shows the outcomes of treatment of toads with chloroxylenol in the ethanol/propanol carrier where the chloroxylenol concentrations tested were 2.5%, 3.75% and 5% (four different carrier mixtures were used in these tests). Axes show weight of toads in grams (x-axis) and minutes to death post-treatment (y-axis).

It was noted that there was increasing variability in the time before extermination following administration of the test pesticidal agent in larger toads (>120 g), irrespective of the treatment administered. The length of time to death observed for some of these animals reflects the length of time taken for cessation of heartbeat, rather than the time taken for loss of movement and responsiveness, which may be more relevant in the field. In these cases, toads appeared to be dead, but with very close observation it was possible to discern the continuing presence of heartbeat. As shown in FIGS. 1 and 2, the times to death between 70 and 120 minutes were not statistically associated with variables such as toad size, carrier formulation, concentration of the pesticidal agent, or any combination thereof.

The application of a variety of control carriers to toads of any size (i.e. ethanol alone, or ethanol in admixture with methanol, propanol or citral) failed to kill any of the 15 toads treated. Once again, inclusion of chloroxylenol in those same carriers resulted in extermination of toads.

In all tests involving the application of the "single-step" composition, all toads were observed to be anaesthetised before death, therefore the "single-step" composition appears to provide a method as effective as the "two-step" method in bringing about the humane extermination of cane toads.

It was also observed that the "single-step" composition resulted in improved efficacy of chloroxylenol as a pesticidal agent. As demonstrated by comparison of the results provided in Tables 1 and 2, the mean times of death of 21 minutes (small toads) and 28 minutes (medium toads), following the "single-step" application of a composition comprising 5% chloroxylenol, 60% ethanol and 40% propanol, was an improvement on the mean times of death of 30 minutes (small toads) and 28 minutes (medium toads) following the application of the "two-step" formulation (i.e. 100% ethanol followed by 5% chloroxylenol in 40% propanol solution). It is suspected, that the improvement in efficacy observed from the "single-step" composition results from the contribution of ethanol to the carrier properties of propanol.

Given the variability in the times before death within treatments, and the associated difficulty in statistically interpreting resulting data, individual observation points for the 92 tests (of 93 in total) in which a lethal outcome was achieved were plotted (see FIGS. 1 and 2). These data report test results of three chloroxylenol concentrations in four propanol-ethanol carrier formulations. In FIG. 1, the data are presented on the basis of the carrier formulation used (so that results for different chloroxylenol concentrations are combined), while in FIG. 2, the same test outcomes are shown on the basis of the chloroxylenol concentration used (so that results for different carrier formulations are combined).

In overview, examination of data in FIGS. 1 and 2 shows that all small toads died within 40 minutes of treatment, with a majority (22/28; 78%) being killed in <30 minutes. In the case of toads of medium size, 25/33 (75%) died within 40 minutes of treatment, and 30/33 (91%) within 60 minutes; all medium sized toads died within 102 minutes of treatment. A smaller number (12/32; 37%) of large toads died within 40 minutes of treatment, but 23/32 (72%) died within 60 minutes, and all but the one noted above died within 120 minutes of treatment.

Further assessment of results in FIG. 1 showed that lines fitted to data points for two of the carrier combinations tested (i.e. 40% propanol with 60% ethanol, and 30% propanol with 70% ethanol) were approximately equivalent in slope, although somewhat displaced with respect to the vertical positions. This may be interpreted as indicating that while the former was slightly more effective than the latter in supporting pesticidal (i.e. killing) action, the relative effectiveness of the two carrier formulations remained constant across the size range of cane toads tested.

In contrast, a line fitted to data points for a third carrier formulation (i.e. 20% propanol with 80% ethanol) showed a higher slope, suggesting that as subject toads become larger, the relative effectiveness of this carrier formulation in supporting pesticidal activity declined in comparison to those of the other two. This outcome is consistent with the fact that the single toad not killed by treatment with the pesticidal agent was the largest toad treated with the 20% propanol-80% ethanol carrier formulation. It is therefore considered that while a 20% propanol-80% ethanol carrier formulation would be effective for use with small toads, its suitability for use with large toads might be more limited.

Assessment of the representation of results provided in FIG. 2 showed that lines fitted to data for the three chloroxylenol concentrations tested (i.e. 2.5%, 3.75% and 5.0%) were approximately equal in slope, although there was again some displacement with respect to the vertical positions. This may be interpreted as indicating, first, that all three concentrations of the pesticidal agent maintain the same relative efficacy of action across the size range of toads tested, second, that the efficacies of the pesticidal agent at 3.75% and 5.0% are essentially identical, and, third, that these concentrations are slightly more active than a concentration of 2.5%.

That said, the fitted line indicates that, in overall terms, even a 2.5% concentration of chloroxylenol can be predicted to kill toads of up to 200 gm weight in less than 60 minutes, albeit with a degree of variation in response of individual cane toads, as observed in the above trials.

Extrapolating these outcomes to the reported size distributions of toads in field populations (which have been calculated to comprise approximately 70%, 25% and 5% small, medium and large toads, respectively, on the basis of data reported by Freeland, W. J. et al., 1986), it can be predicted that use of the pesticidal composition and method disclosed herein, would enable about 91% of all toads to be killed within 40 minutes of treatment, and 97% within 60 minutes. Further, with the adoption of an appropriate carrier formulation, as discussed above, the method would be generally expected to kill all toads within 120 minutes of treatment.

Example 3

Testing Efficacy of a Formulation Delivered by Aerosol Spray Under Field Conditions The tests conducted in this example involved spray application of a composition in accordance with the present invention on cane toads under field conditions in northern Queensland, Australia.

Materials and Methods

Trial 3

A detailed series of tests was performed with a composition comprising 4% (w/v) chloroxylenol in 30% (v/v) isopropanol and 67% (v/v) ethanol, and containing in addition an alcohol-soluble fragrance agent (citral; CAS 5392-40-5) at a concentration of 0.5% (v/v). This mixture was dispensed as an aerosol spray from a pressurised spray can of the type typically used in domestic households for the delivery of a range of materials including, for example, pesticidal sprays. The spray cans were manufactured at Spraypack Pty Ltd, Revesby, NSW, Australia.

Field trials were undertaken in the widely separated locations of Townsville and Mareeba. Toads used in Townsville were sourced from within the town, while in the case of Mareeba, toads were collected and transported to the test site from source areas within the surrounding region.

In each test, the subject toad was weighed, then treated with a brief (~1-3 second) topical spray application of the formulation onto its dorsal surface. The duration of the spray was subjectively matched to the size of the toad. Two treatment methodologies were tested, the first being a single continuous spray ("single shot"), and the other being two shorter sprays ("double shot"), with the second spray typically administered some 15-90 seconds after the first, when toad movement had either ceased or become lethargic in manner.

Spray cans were weighed before and after each test administration so that individual dosages could be quantified. Each instance of spray application was recorded by digital video, and the recording was subsequently analysed to determine factors such as the qualitative response of animals to treatment, and occurrence/duration of movement of animals after treatment.

Results and Discussion

Table 5 summarises the outcomes of the Trial 3 tests on 43 cane toads in field settings.

Toads administered the "double shot" treatment ranged in size from 25-320 gm. Analysis of results for "double shot" treatments showed that there was no significant difference in the relative amounts of spray formulation applied (i.e. grams of spray used per gram weight of toad) in the two geographically-separated trials ($t_{31}=1.5$; $p=0.1$).

Having established the equivalence of treatment of toads at the two locations, further analyses of results showed that there was no significant difference between the two locations with respect to the total lengths of time that toads continued to move after "double shot" treatment with the formulation ($t_{29}=0.06$; $p=0.9$). Data from both locations were thus pooled for subsequent analyses; these showed that the mean duration of continued movement post-treatment ($\pm$S.E.; $n=31$) was 54.3±7.3 seconds. As shown in Table 5, the observed range of continued movement duration was 5-127 seconds.

Figure 3:
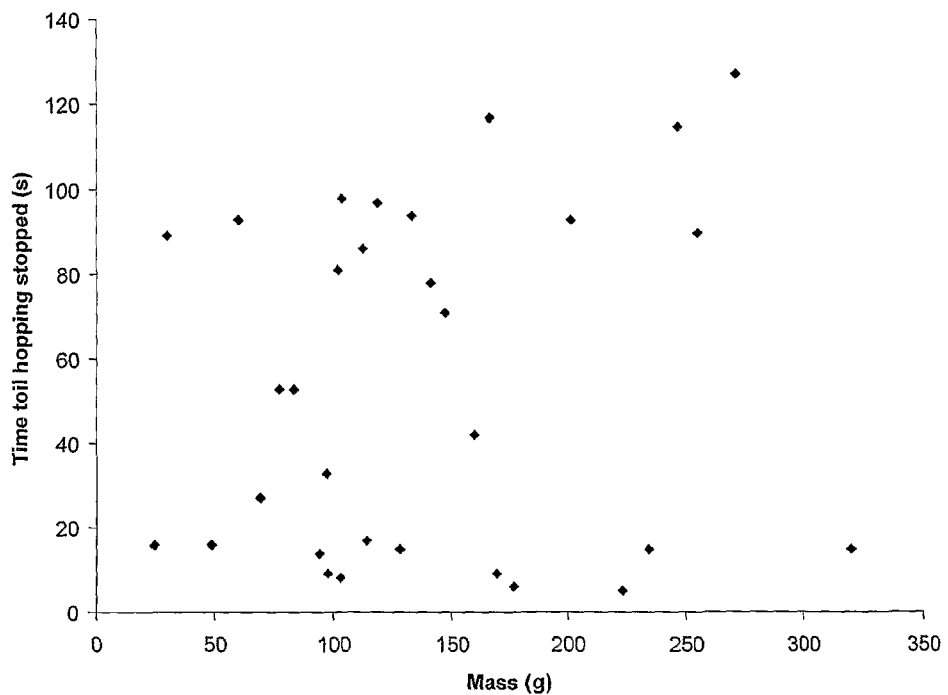
FIG. 3 provides a scatter plot of the duration of cane toad hopping (seconds; y-axis) after treatment with an aerosol composition of 67% ethanol, 30% isopropanol, 4% chloroxylenol and 0.5% citral against the individual mass of the treated cane toads (grams; x-axis).

As shown in FIG. 3, there was no significant relationship between the size of treated toads and the post-administration duration of their movement. The qualitative assessment of the duration of movement of toads was largely related to their instinctive attempt to reach a point of "cover" after feeling the topical application of the spray, and that they continued to move either until subjectively suitable cover was reached or until they were overcome by the effect of the formulation.

Further analysis of the "double shot" results showed that there was also no significant difference between the trial locations with respect to the time to death of toads after treatment ($t_{31}=1.8$; $p=0.07$). Data from both locations were thus pooled for combined assessment, which showed that the mean time to death after "double shot" treatment (±S.E.; $n=33$) was 45.9±3.9 minutes. As shown in Table 5, the range of times to death was 10-132 minutes.

Toads administered the "single shot" treatment ranged in size from 65-120 gm. Analysis of data for the "single shot" trials showed that there was no significant difference in the relative amounts of spray formulation applied (i.e. grams of spray used per gram weight of toad) in the two geographically separated trials ($t_9=0.7$; $p=0.5$).

The low sample sizes in the "single shot" tests meant that analyses of "between location" effects were of relatively low power. In this context, analysis showed that the continued duration of movement of toads post-administration differed between the two locations ($t_8=2.3$; $p<0.001$), with toads in Townsville trials moving for a shorter time than those at Mareeba; mean times (±SE) were 28.8±9.3 seconds ($n=6$) for the former, and 89.0±20.1 seconds ($n=3$) for the latter. As shown in Table 5, the observed range of continued movement duration across both sites was 8-117 seconds.

No significant difference was observed between the times to death of "single shot" treated toads at the two locations ($t_9$=1.9; p=0.09). Data from both locations were thus pooled for combined analysis, which showed that the mean time to death after treatment (±S.E.; n=10) was 52.4±5.8 minutes. As shown in Table 5, the range of times to death was 33-88 minutes.

Using the pooled (across locations) data, comparison of times to death for animals administered the formulation by either "single-" or "double-shot" treatments showed no significant difference between the two methods ($t_{41}$=0.8; p=0.4).

Figure 4:
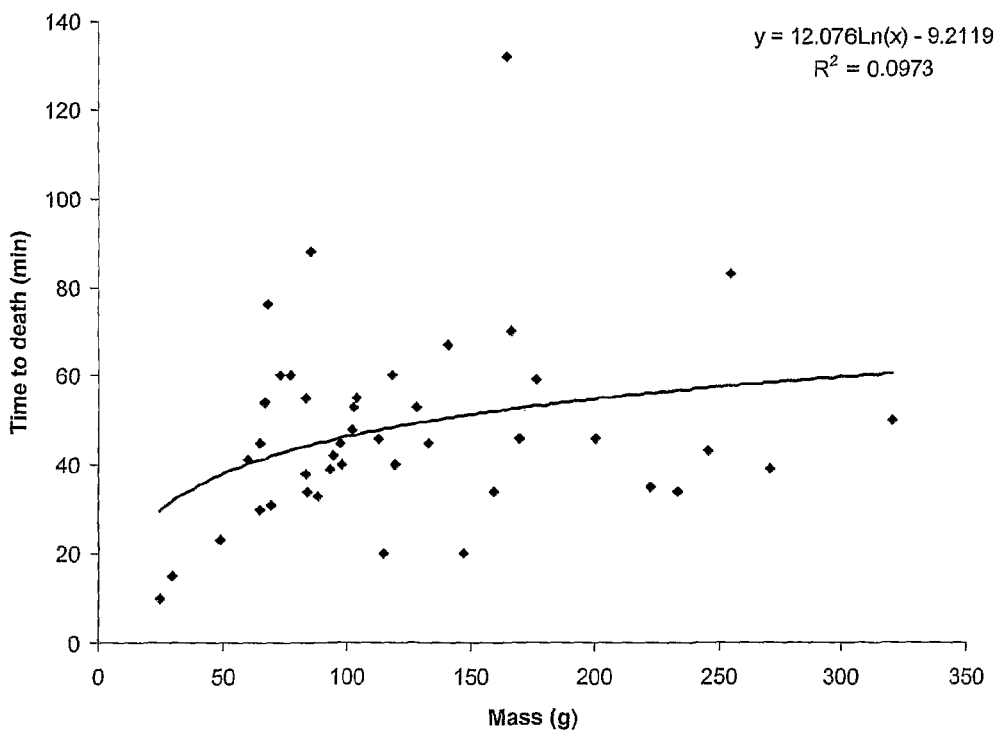
FIG. 4 provides a scatter plot of the time to death (minutes; y-axis) after treatment of cane toads with an aerosol composition of 67% ethanol, 30% isopropanol, 4% chloroxylenol, and 0.5% citral shown against the individual mass of the treated cane toads (grams; x-axis).

Analysis of times to death for all treated toads ("single-" and "double-shot" data) showed no significant relationship between the size of the toad and its time to death ($r^2$=0.097; FIG. 4). This result is presumed to reflect the fact that in this field trial situation the amount of spray applied to each toad was subjectively matched to the size of the animal, as might be expected for the pattern of end-user use of any product based on the compositions. It was noted that both this methodology and outcome contrasted with those of the laboratory trials, in which the treatment dose was constant regardless of subject size, and which consequently produced the time-to-death dose-relationship outcomes shown in FIGS. 1 and 2.

In summary, the administration of the composition via aerosol delivery was 100% effective in killing cane toads in field trial settings in Australia, irrespective of the specific technique of administration, and across a sample of animals differing in size by more than an order of magnitude (25-320 gm) and sourced from two widely separated (~275 km) geographic locations.

TABLE 5

Outcomes of treatment of cane toads under field conditions with 4.0% chloroxylenol aerosol test formulation

| Trial location | test | toad ID | weight (gm) | sex | gm spray (total) | gm spray/ gm toad | movement duration p.a. (sec) | time to death (min) |
|---|---|---|---|---|---|---|---|---|
| Mareeba | single shot | 297 | 120 | M | 10.9 | 0.091 | 100 | 40 |
| | | 299 | 93 | F | 8.9 | 0.096 | 50 | 39 |
| | | 300 | 84 | F | 15.8 | 0.188 | 117 | 34 |
| Townsville | single shot | 313 | 68 | F | 7.2 | 0.106 | 30 | 76 |
| | | 314 | 88 | M | 7.9 | 0.090 | 13 | 33 |
| | | 315 | 67 | F | 8.2 | 0.122 | 70 | 54 |
| | | 316 | 83 | F | 7.6 | 0.092 | 8 | 55 |
| | | 317 | 85 | F | 5.6 | 0.066 | n.a. | 88 |
| | | 318 | 73 | F | 9.3 | 0.127 | 36 | 60 |
| | | 319 | 65 | F | 8.8 | 0.135 | 16 | 45 |
| Mareeba | double shot | 271 | 133 | M | 11.2 | 0.084 | 94 | 45 |
| | | 272 | 128 | F | 7.6 | 0.059 | 15 | 53 |
| | | 273 | 167 | M | 9.1 | 0.054 | 117 | 70 |
| | | 274 | 165 | F | 10.9 | 0.066 | n.a. | 132 |
| | | 275 | 234 | F | 13.3 | 0.057 | 15 | 34 |
| | | 276 | 223 | M | 20.6 | 0.092 | 5 | 35 |
| | | 277 | 246 | F | 20.5 | 0.083 | 115 | 43 |
| | | 278 | 201 | F | 13.4 | 0.067 | 93 | 46 |
| | | 284 | 102 | n.a. | 8.3 | 0.081 | 81 | 48 |
| | | 285 | 113 | M | 9.1 | 0.081 | 86 | 46 |
| | | 286 | 94 | M | 9.2 | 0.098 | 14 | 42 |
| | | 287 | 69 | M | 8.0 | 0.116 | 27 | 31 |
| | | 288 | 98 | F | 7.1 | 0.072 | 9 | 40 |
| | | 289 | 65 | F | 12.7 | 0.195 | n.a. | 30 |
| | | 290 | 160 | F | 11.2 | 0.070 | 42 | 34 |
| | | 291 | 177 | F | 14.3 | 0.081 | 6 | 59 |
| | | 292 | 170 | M | 13.4 | 0.079 | 9 | 46 |
| | | 293 | 141 | F | 15.6 | 0.111 | 78 | 67 |
| | | 294 | 255 | F | 14.3 | 0.056 | 90 | 83 |
| | | 295 | 271 | F | 17.3 | 0.064 | 127 | 39 |
| | | 296 | 320 | F | 19.3 | 0.060 | 15 | 50 |
| Townsville | double shot | 301 | 77 | F | 10.0 | 0.130 | 53 | 60 |
| | | 302 | 104 | M | 7.3 | 0.070 | 98 | 55 |
| | | 303 | 97 | M | 7.9 | 0.081 | 33 | 45 |
| | | 304 | 115 | F | 10.8 | 0.094 | 17 | 20 |
| | | 305 | 60 | M | 7.3 | 0.122 | 93 | 41 |
| | | 306 | 119 | F | 6.8 | 0.057 | 97 | 60 |
| | | 307 | 83 | M | 6.0 | 0.072 | 53 | 38 |
| | | 308 | 103 | F | 5.6 | 0.054 | 8 | 53 |
| | | 309 | 147 | F | 9.7 | 0.066 | 71 | 20 |
| | | 310 | 49 | F | 5.6 | 0.114 | 16 | 23 |
| | | 311 | 30 | F | 6.2 | 0.207 | 89 | 15 |
| | | 312 | 25 | M | 4.3 | 0.172 | 16 | 10 |

Example 4

Laboratory Trials of Aerosol-Delivered Formulations with Toad and Frog Pests in North America The tests conducted in this example involved spray application of a composition in accordance with the present invention on cane toads and Cuban tree frogs under laboratory conditions in Florida, USA.

Materials and Methods

Trial 4

A detailed series of tests was done with a composition comprising 4% (w/v) chloroxylenol in 30% (v/v) isopropanol and 67% (v/v) ethanol, and containing in addition an alcohol-soluble fragrance agent (citral; CAS 539240-5) at a concentration of 0.5% (v/v). This composition was tested on both cane toads (n=13) and Cuban tree frogs (n=15). Additional tests on Cuban tree frogs (n=9) were done using a composition comprising 3.5% (w/v) chloroxylenol in 30% (v/v) isopropanol, 67% (v/v) ethanol and 0.5% (v/v) citral. Both compositions were dispensed as aerosol sprays from pressurised spray cans (Spraypack Pty Ltd, Revesby, NSW, Australia) of the type typically used in domestic households for delivery of a range of materials including pesticidal sprays.

Cane toads were hand-collected from a suburban backyard in West Palm Beach, Fla. Cuban tree frogs were collected in Tampa, Fla., and nearby suburban areas (Plant City and Bealsville), from PVC 'habitat tubes' in which the frogs had found shelter.

In each test, the subject animal was weighed, then treated with a single brief (~1-3 second) topical spray application of the formulation onto its dorsal surface. The duration of the spray was subjectively matched to the size of the animal. Spray cans were typically weighed before and after each test administration so that individual dosages could be quantitated.

Results and Discussion
Cane Toad Trial

Responses of Florida-sourced cane toads to spray treatment were highly consistent with previously observed responses of cane toads under laboratory and field conditions in Australia. Thus, after a short period of movement, toads typically adopted a flattened posture on the floor of the container, and thereafter remained motionless, usually with eyes closed. Table 6 reports the outcomes of treatment of 13 cane toads by application of the aerosol spray. As shown, twelve of the animals died as a result of treatment, and one was euthanased. The mean size of animals killed by treatment (±standard error; S.E.) was 73.3±11.3 gm, with a range of 14-145 gm. The mean time to death (±S.E.) of these animals was 35.8±4.7 minutes, with a range of 9-59 minutes.

Statistical analysis showed that when the lethally-treated Florida test population (n=12) was compared with the population from Queensland treated with a "single shot" of the same formulation (n=10; see Table 5) there was no significant difference either in the sizes of animals in the two samples (t=0.697, d.f.=20, p=0.49) or the relative amounts of spray formulation each received (i.e. gm spray used per gram weight of toad; t=0.06, d.f.=20, p=0.95). There was, however, a marginally significant difference in times to death for toads in the two samples, with those from Florida dying slightly more quickly than those from Queensland (mean time of 35.8 minutes, compared to a mean time of 52.4 minutes for those from Queensland; t=2.26, d.f.=20, p=0.04).

Noting that toads were tested under laboratory conditions in Florida and field conditions in Queensland, it is difficult to draw a strict conclusion from this latter comparison. Nevertheless, it is apparent that toads in Florida, USA, are, at the least, as susceptible to control by the test formulation as those in Queensland, Australia.

One Florida-sourced toad treated with the same formulation was euthanased. This toad (#337) was treated with a much shorter spray than intended, providing a substantially lower dose than intended (0.043 gm spray/gm weight toad), or than applied to the 12 animals killed by treatment (mean±SE=0.110±0.014 gm spray/gm weight toad). This toad was euthanased at the expiration of the period allowed for testing (3 hours). At that time, the only visible sign of life was a near-imperceptible heartbeat; it is considered that the animal would have died shortly thereafter. Taking outcomes of treatments of toads #333, 336, 337 and 340 (Table 6) in combination, it can be considered that a minimum dosage of about 0.060-0.070 gm spray per gm weight of toad represents an appropriate treatment regime for this population.

Cuban Tree Frog Trials

Tables 7 and 8 report the outcomes of treatment of a total of 24 Cuban tree frogs (*Osteopilus septentrionalis*) by application of spray formulations of the claimed composition.

The effect of treatment on Cuban tree frogs was very similar to that described for cane toads. Animals responded immediately to application of the spray by vigorous hopping for a short period (<1 minute), then typically collapsed into an uncoordinated position on the floor of the test container, and did not move again.

Table 7 reports details of treatment of 15 frogs with a composition containing 4.0% chloroxylenol. Fourteen of the frogs were in the size range 1.6 to 19.5 gm, with the mean size (±S.E.) of this group being 9.1±1.4 gm. These animals received a mean dosage (±S.E.) of 0.396±0.081 gm spray per gm body weight. All frogs were killed by the treatment; death occurred in a mean (±S.E.) time of 9.6±1.1 minutes, with a range of 7-22 minutes.

The fifteenth frog (#326) was substantially larger (41.0 gm), and near the upper end of the size range for this species. This animal received a dosage of 0.206 gm spray per gm body weight; its response to treatment was identical to those of other animals, with cessation of jumping activity occurring within 60 seconds of treatment. The animal died in 102 minutes; for the latter 82 minutes of this period the only visible sign of life was an increasingly faint heartbeat. No other individual of this body size was available for testing, so beyond the fact that the treatment was lethal to the animal it is not possible to make further assessments. We note that for large individuals of this species, a second spray of the formulation, as has previously been used with cane toads (see Trial 3), may be useful.

Table 8 reports details of treatment of 9 frogs with a composition containing 3.5% chloroxylenol. Frogs were in the size range 1.7 to 11.2 gm, with the mean size (±S.E.) of this group being 5.9±0.9 gm. These animals received an estimated mean dosage (±S.E.) of 0.333±0.097 gm spray per gm body weight. All the frogs were killed by the treatment; death occurred in a mean (±S.E.) time of 9.3±1.3 minutes, with a range of 5-16 minutes.

On the basis of these data, it can be concluded that the Cuban tree frog is susceptible to compositions of the present invention, and that products based on the composition will have utility for their management.

TABLE 6

Outcomes of treatment of cane toads under laboratory conditions in Florida with 4.0% chloroxylenol aerosol test formulation

| toad ID | weight (gm) | sex | gm spray (total) | gm spray/ gm toad | time to death (min) | notes |
|---|---|---|---|---|---|---|
| 329 | 28 | F | 5.70 | 0.204 | 29 | |
| 330 | 14 | F | 1.35 | 0.096 | 9 | |
| 331 | 25 | M | 5.20 | 0.208 | 18 | |
| 332 | 110 | M | 10.90 | 0.099 | 44 | |
| 333 | 104 | F | 7.40 | 0.071 | 40 | |
| 335 | 93 | F | 9.75 | 0.105 | 56 | |
| 336 | 92 | F | 6.25 | 0.068 | 44 | |
| 337 | 71 | M | 3.05 | 0.043 | n.a. | euthanased |
| 338 | 53 | F | 4.55 | 0.086 | 38 | |
| 339 | 145 | F | 13.60 | 0.094 | 47 | |
| 340 | 86 | M | 4.90 | 0.057 | 59 | |

TABLE 6-continued

Outcomes of treatment of cane toads under laboratory conditions in Florida with 4.0% chloroxylenol aerosol test formulation

| toad ID | weight (gm) | sex | gm spray (total) | gm spray/ gm toad | time to death (min) | notes |
|---|---|---|---|---|---|---|
| 341 | 72 | F | 7.65 | 0.106 | 12 | |
| 342 | 58 | F | 7.40 | 0.128 | 34 | |

TABLE 7

Outcomes of treatment of Cuban tree frogs under laboratory conditions in Florida with 4.0% chloroxylenol aerosol test formulation

| frog ID | weight (gm) | gm spray (total) | gm spray/ gm toad | time to death (min) |
|---|---|---|---|---|
| 320 | 1.6 | 1.90 | 1.188 | 9 |
| 321 | 4.5 | 2.50 | 0.556 | 10 |
| 322 | 2.9 | 1.45 | 0.500 | 8 |
| 324 | 13.5 | 3.15 | 0.233 | 8 |
| 326 | 41.0 | 8.45 | 0.206 | 102 |
| 327 | 5.5 | 1.65 | 0.300 | 14 |
| 328 | 2.7 | 2.40 | 0.889 | 7 |
| 343 | 15.5 | 2.80 | 0.181 | 8 |
| 344 | 16.5 | 2.75 | 0.167 | 7 |
| 345 | 19.5 | 2.45 | 0.126 | 22 |
| 346 | 11.5 | 3.70 | 0.322 | 11 |
| 347 | 11.0 | 2.65 | 0.241 | 8 |
| 348 | 10.5 | 2.60 | 0.248 | 7 |
| 349 | 8.5 | 2.75 | 0.324 | 7 |
| 350 | 9.0 | 2.40 | 0.267 | 8 |

TABLE 8

Outcomes of treatment of Cuban tree frogs under laboratory conditions in florida with 3.5% chloroxylenol aerosol test formulation

| frog ID | weight (gm) | gm spray (total) | gm spray/ gm toad | time to death (min) |
|---|---|---|---|---|
| 351 | 1.7 | 1.65 | 0.971 | 7 |
| 352 | 6.5 | 1.50 | 0.231 | 16 |
| 353 | 3.7 | na | na | 7 |
| 354 | 2.5 | na | na | 14 |
| 355 | 5.2 | 2.30 | 0.442 | 8 |
| 356 | 8.1 | 2.10 | 0.259 | 5 |
| 357 | 11.2 | 2.80 | 0.250 | 12 |
| 358 | 5.4 | 2.25 | 0.417 | 7 |
| 359 | 4.4 | 1.75 | 0.398 | 5 |

Although a preferred embodiment of the method of the present invention has been described in the foregoing detailed description, it will be understood that the invention is not limited to the embodiment disclosed, but is capable of numerous rearrangements, modifications and substitutions without departing from the scope of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

REFERENCES

1. Lever, C. 2001. The Cane Toad: The History and Ecology of a Successful Colonist. Westbury Publishing, West Yorkshire, UK
2. Doody, J S, Green, B, Sims, R and Rhind, D. 2006. Initial impacts of invasive cane toads (*Bufo marinus*) on predatory lizards and crocodiles. Pp 33-41; Molloy, K L & Henderson, W R (eds). 2006. Science of Cane Toad Invasion and Control. Proceedings of the Invasive Animals CRC/CSIRO/Qld NRM&W Cane Toad workshop, Brisbane 2006. Invasive Animals Research Centre, Canberra. ISBN 0-9775707-2-X.
3. Youth, H. 2005. Toxic Toads and Tyrannical Treefrogs ZooGoer 34:3. Smithsonian National Zoological Park. http://nationalzoo.si.edu/Publications/ZooGoer/2005/3/amphibiansidebar.cfm
4. Roberts, B K, Aronsohn, M G, Moses, B L, Burk, R L, Toll, J and Weeren, F R. 2000. *Bufo marinus* intoxication in dogs: 94 cases (1997-1998). J AM Vet Med Assoc. 216, 1941-1944.
5. Reeves, M P. 2004. A retrospective report of 90 dogs with suspected cane toad (*Bufo marinus*) toxicity. Aust Vet J. 82, 608-611.
6. Johnson, S. A. 2007. The Cuban Treefrog (*Osteopilus septentrionalis*) in Florida. University of Florida, Institute of Food and Agricultural Sciences Report WEC218.
7. Knapp, W. W. 2007. Frogs and Toads of Georgia.
8. International Union for the Conservation of Nature, Invasive Species Specialist Group "100 of the World's Worst Invasive Alien Species"
9. Wilson, A. 2006. Attack of the Toads. Pp 31-33, Weekend Australian Magazine. 22 Jul. 2006.
10. Sawyer, G. 2006. Frogwatch trapping Report. Pp 61-72; Molloy, K L & Henderson, W R (eds). 2006. Science of Cane Toad Invasion and Control. Proceedings of the Invasive Animals CRC/CSIRO/Qld NRM&W Cane Toad workshop, Brisbane 2006. Invasive Animals Research Centre, Canberra. ISBN 0-9775707-2-X.
11. Anon. Control of Coqui Frogs in Hawaii. College of Tropical Agriculture and Human Resources.
12. Crayon, J. J. 2005. Ecology of *Rana catesbeiana*.
13. Giovanelli, J G R, Haddad, C F B and Alexandrino, J. 2007. Predicting the potential distribution of the alien invasive American bullfrog (*Lithobates catesbeinanus*) in Brazil. Biological Invasions 10.1007/s10530-007-9154-5
14. Ficetola G F, Coïc, C, Detaint, M, Berroneau, M, Lorvelec, O and Miaud, C. 2007. Patterns of distribution of the American bullfrog *Rana catesbeiana* in Europe. Biological Invasions 9, 767-772.
15. Freeland, W J, Delvinquier, B L J and Bonnin, B. 1986. Decline of cane toad, *Bufo marinus*, populations: status of urban toads. Aust Wildl. Res. 13, 597-601.

The invention claimed is:
1. A composition for killing amphibians comprising:
(i) 3.75% (w/v) to 10% (w/v) of 4-chloro 3,5-dimethyl phenol; and
(ii) ethanol at a concentration of greater than 50% (v/v), and

(iii) methanol, propanol or isopropanol, or a mixture thereof.

2. The composition of claim 1, further comprising at least one compound selected from the group consisting of diluents, solvents, thickeners, stabilisers, propellants, fragrants, insecticides, insect repellants, amphibian attracting agents and canine or feline repelling agents.

3. The composition of claim 1 wherein said 4 chloro 3,5-dimethyl phenol is present at a concentration of between 3.75% (w/v) and 6.5% (w/v), ethanol is present at a concentration of between 55% (v/v) and 80% (v/v), and isopropanol is present at a concentration of between 20% (v/v) and 40% (v/v).

4. The composition claim 1 comprising:
   (i) 4-chloro 3,5-dimethyl phenol at a concentration of 4.0% (w/v);
   (ii) ethanol at a concentration of about 67% (v/v);
   (iii) isopropanol at a concentration of about 30% (v/v); and
   (iv) citral at a concentration of about 0.5% (v/v).

* * * * *